US008043339B2

(12) United States Patent
Hudgins et al.

(10) Patent No.: US 8,043,339 B2
(45) Date of Patent: Oct. 25, 2011

(54) FLEXIBLE MEMBER FOR USE IN A SPINAL COLUMN AND METHOD FOR MAKING

(75) Inventors: Robert Garryl Hudgins, Monticello, MN (US); Thomas O. Viker, Arden Hills, MN (US); Hugh D. Hestad, Edina, MN (US); David Mowry, Aliso Viejo, CA (US); Jack A. Dant, St. Paul, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 1015 days.

(21) Appl. No.: 11/923,340

(22) Filed: Oct. 24, 2007

(65) Prior Publication Data

US 2009/0112265 A1 Apr. 30, 2009

(51) Int. Cl.
*A61B 17/70* (2006.01)

(52) U.S. Cl. .......................................... 606/255; 606/259

(58) Field of Classification Search .................. 606/246, 606/253–263, 279; 600/30; 623/2.37
See application file for complete search history.

(56) References Cited

U.S. PATENT DOCUMENTS

| 4,743,260 | A | | 5/1988 | Burton | |
|---|---|---|---|---|---|
| 5,540,688 | A | * | 7/1996 | Navas | 606/266 |
| 6,986,771 | B2 | | 1/2006 | Paul et al. | |
| 7,326,210 | B2 | * | 2/2008 | Jahng et al. | 606/86 A |
| 7,763,052 | B2 | * | 7/2010 | Jahng | 606/254 |
| 2003/0061839 | A1 | * | 4/2003 | Kost | 66/192 |
| 2005/0203517 | A1 | * | 9/2005 | Jahng et al. | 606/61 |
| 2005/0277922 | A1 | * | 12/2005 | Trieu et al. | 606/61 |
| 2006/0009768 | A1 | | 1/2006 | Ritland | |
| 2006/0155279 | A1 | * | 7/2006 | Ogilvie | 606/61 |
| 2007/0129729 | A1 | * | 6/2007 | Petit et al. | 606/61 |
| 2008/0234744 | A1 | * | 9/2008 | Zylber et al. | 606/264 |
| 2008/0269804 | A1 | * | 10/2008 | Holt | 606/254 |

FOREIGN PATENT DOCUMENTS

| WO | 03/047441 A1 | 6/2003 |
|---|---|---|
| WO | 2004096066 A2 | 11/2004 |
| WO | 2007087476 A1 | 8/2007 |
| WO | 2007097905 A2 | 8/2007 |
| WO | 2007127604 A2 | 11/2007 |

OTHER PUBLICATIONS

Cloth, Merriam Webster dictionary, accessed Apr. 4, 2011 http://www.merriam-webster.com/dictionary/cloth.*
Fabric, Merriam-Webster Dictionary, accessed Apr. 4, 2011 http://www.merriam-webster.com/dictionary/fabric.*

* cited by examiner

*Primary Examiner* — Eduardo C. Robert
*Assistant Examiner* — Steven Cotroneo
(74) *Attorney, Agent, or Firm* — Seager Tufte & Wickhem LLC

(57) ABSTRACT

The present invention relates to flexible members for stabilizing a spinal column and methods for making the flexible members. In one embodiment, a flexible member comprises an inner elastomeric member and an outer fabric layer situated securely around the inner elastomeric member. The inner elastomeric member has a first elasticity to provide the flexible member with a desired flexibility. In another embodiment, the flexible member includes an outer covering that defines an outer elastomeric member. The outer elastomeric member may be situated securely around the outer fabric layer with the inner elastomeric member, the outer fabric layer, and the outer elastomeric member having the common lengthwise axis and defining the body including the opposing first and second ends. The outer elastomeric member may have a second elasticity that is less than the first elasticity.

9 Claims, 4 Drawing Sheets

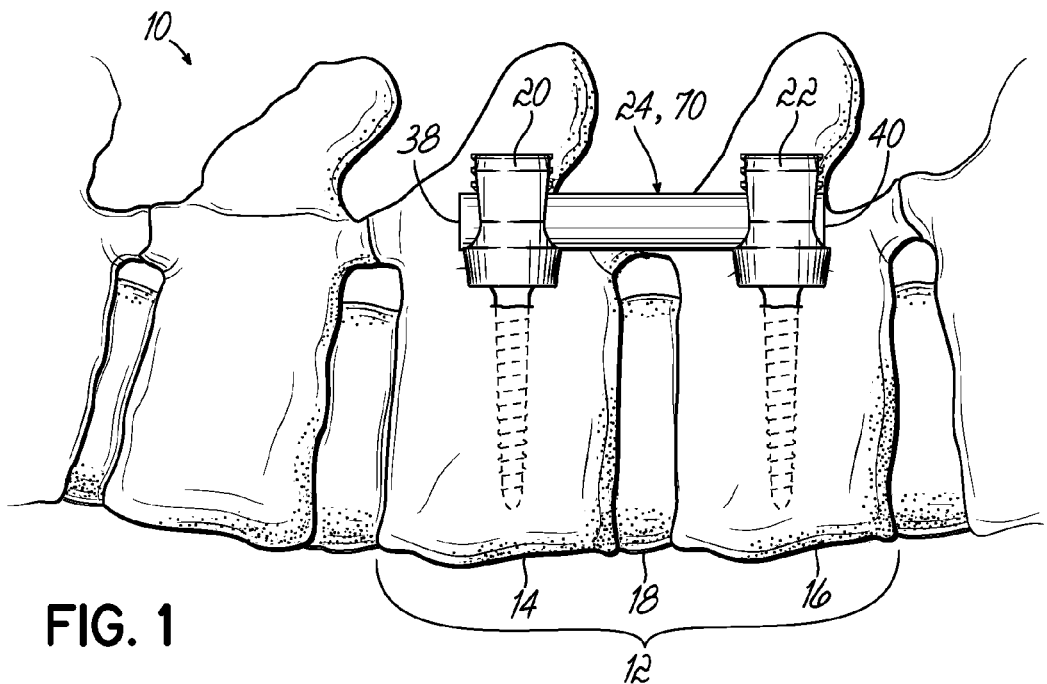
FIG. 1
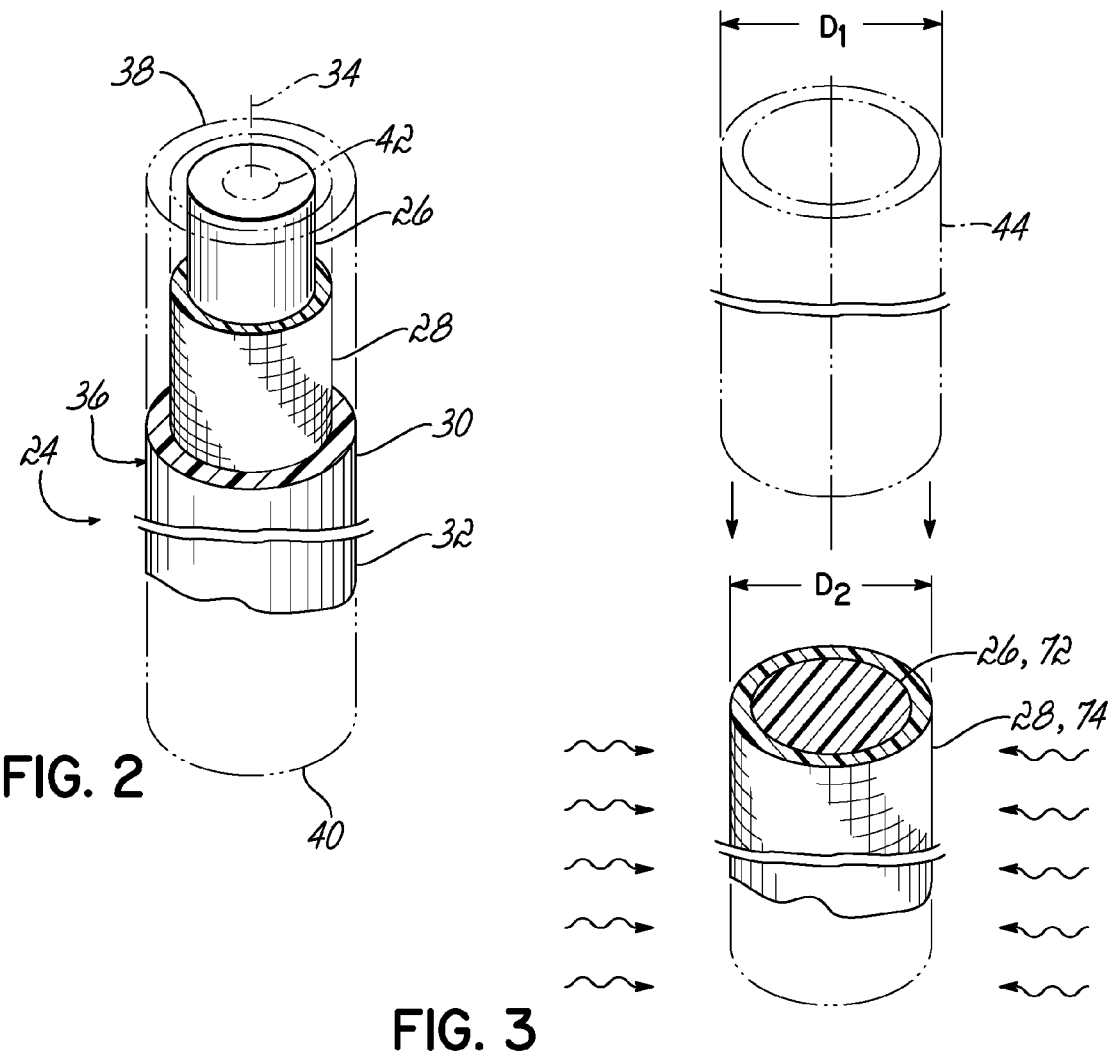
FIG. 2
FIG. 3

FLEXIBLE MEMBER FOR USE IN A SPINAL COLUMN AND METHOD FOR MAKING

FIELD OF THE INVENTION

The present invention relates to spinal column treatment, and, more particularly, to flexible members for stabilizing motion segments therein.

BACKGROUND OF THE INVENTION

The spine includes a series of joints or motion segments. The components of each motion segment include two adjacent vertebrae and their apophyseal joints, an intervertebral disc, and connecting ligamentous tissue. Each motion segment is capable of flexion, extension, lateral bending, and translation. Each component of the motion segment contributes to the mechanical stability of that joint. Overall, the motion segments enable the familiar kinematic motion of the spinal column.

Components of a motion segment that move out of position, become damaged, deteriorate, or are disordered in some fashion, can lead to serious pain. Furthermore, these disorders may lead to injury to other components of the spine. Depending upon the degree of disorder or damage that has occurred, treatment may include fusing the components of the motion segment together.

Fusion procedures include rigid stabilization of one or more motion segments, i.e., immobilization of the motion segment. Fusing usually involves fixation of a metallic rod, plate, or other rigid member to components of the disordered motion segment to promote fusion within and between these components. However, fusing motion segments may lead to other problems. Simply put, fusion results in a loss of mobility in that motion segment. The lost mobility in the fused motion segment transfers the required movement to other, non-fused motion segments. Adjacent, non-fused motion segments experience the greatest transfer of the demand for motion. Added demand increases the stress on the non-fused motion segments, and, consequently, causes non-fused motion segments to deteriorate. Therefore, loss of motion in one motion segment may contribute to or even cause disorders in the motion segments above and below the fused motion segment.

Thus, a stabilization member that permits limited motion of the disordered motion segment and which reduces the demand for motion on adjacent motion segments is needed.

SUMMARY OF THE INVENTION

The present invention provides a flexible member for use in stabilizing a spinal column and a method for making the flexible member, and a method for treating the spinal column utilizing the flexible member. In one embodiment, the flexible member comprises n inner elastomeric member and an outer fabric layer situated securely around the inner elastomeric member. The inner elastomeric member and the outer fabric layer have a common lengthwise axis and define a body including opposing first and second ends. Each opposing end may be configured for cooperation with an anchor member. The inner elastomeric member has a first elasticity to provide the flexible member with a desired flexibility. In another embodiment, the flexible member includes an outer covering that defines an outer elastomeric member. The outer elastomeric member may be situated securely around the outer fabric layer with the inner elastomeric member, the outer fabric layer, and the outer elastomeric member having the common lengthwise axis and defining the body including the opposing first and second ends. In another embodiment, the outer elastomeric member has a second elasticity that is less than the first elasticity.

In another embodiment, the flexible member comprises an elongated core member including a plurality of spaced-apart annular protrusions oriented perpendicular to a lengthwise axis with spacing between pairs of protrusions defining a circumferential groove. A plurality of ring-shaped members with one each of the plurality of ring-shaped members securely is situated about the elongated core member. The respective circumferential groove and adjacent corresponding annular protrusions define a body. The body includes opposing first and second ends, with each opposing end configured for cooperation with an anchor member. The annular protrusions and core member define a monolith having a first elasticity and the ring-shaped members having a second elasticity that is different than the first elasticity to provide the flexible member with a desired flexibility.

In yet another embodiment, the flexible member comprises an elongated polymeric member and an outer nitinol member situated securely around the polymeric member. The polymeric member and the nitinol outer member having a common lengthwise axis and define a body including opposing first and second ends. Each opposing end is configured for cooperation with an anchor member. The polymeric member further has a first elasticity and the outer nitinol member has a second elasticity different than the first elasticity to provide the flexible member with a desired flexibility.

Also provided according to the principles disclosed herein is a method for making the flexible member. In one embodiment, the method comprises providing an inner elastomeric member having a first elasticity to provide the flexible member with a desired flexibility, placing a fabric member about the inner elastomeric member, and shrinking the fabric member around the inner elastomeric member to securely situate the fabric member therearound thereby defining an outer fabric layer. The inner elastomeric member and the outer fabric layer have a common lengthwise axis and define a body including opposing first and second ends. Each opposing end is configured for cooperation with an anchor member.

In another embodiment, a method for making a flexible member comprises forming an elongated core member with spaced-apart circumferential grooves about a lengthwise axis thereof to define a plurality of spaced-apart annular protrusions oriented perpendicular to the lengthwise axis, filling the grooves with a liquefied material, and solidifying the liquefied material to provide a plurality of ring-shaped members with one each of the plurality of ring-shaped members securely situated about the elongated core member within a respective circumferential groove and adjacent corresponding annular protrusions thereby defining a body.

In another embodiment, a method for making a flexible member comprises aligning a plurality of spaced-apart ring-shaped members, where each of the ring-shaped members includes a central aperture and is oriented perpendicular to a lengthwise axis. In addition the method comprises filling the spaces between the spaced-apart ring-shaped members and apertures with a liquefied material and then solidifying the liquefied material to define a body that includes an elongated core member. The elongated core member has a plurality of spaced apart annular protrusions and one each of the plurality of ring-shaped members is securely situated about the elongated core member within a respective circumferential groove and adjacent corresponding annular protrusions.

In accordance with the principles of the invention, a method for treating the spine of a patient is provided. The method comprises assessing the patient's spine, providing a plurality of implants of different elastic characteristics, selecting one or more of the plurality of implants based on the assessment of the patient's spine and the elastic characteristics of the implants, and coupling the one or more implants to anchor members, the anchor members engaging the patient's spine. The implants each comprise an inner portion of one elastomeric material and an outer portion of a second elastomeric material.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

FIG. 1 is a partial side view of a spinal column with two anchor members fixed into adjacent vertebra separated by a intervertebral disc and one embodiment of a flexible member secured at opposing ends by the anchor members;

FIG. 2 is a partial perspective view of one embodiment of the flexible member having an inner elastomeric member formed with an outer fabric layer and an outer elastomeric member with a portion of each of the fabric layer and elastomeric jacket removed;

FIG. 3 is a diagrammatic perspective view of one method of forming the outer fabric layer around the inner elastomeric member;

DETAILED DESCRIPTION

Figure 4:
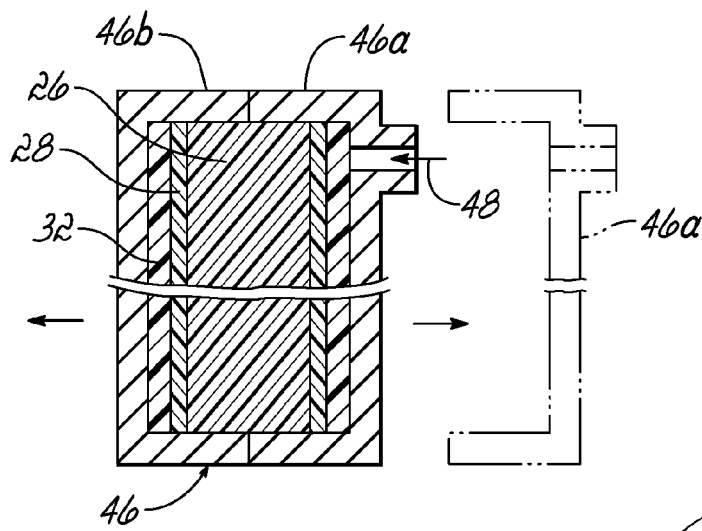
FIG. 4 is a diagrammatic cross-sectional view of one method of forming the outer elastomeric member around the outer fabric layer and the inner elastomeric member of FIG. 2 with a mold.

FIG. 1 depicts a portion of a spinal column 10 having a motion segment 12. Each motion segment 12 has adjacent vertebrae 14, 16 with an intervertebral disc 18 positioned therebetween. A first anchor member 20 is secured in one vertebra 14 and a second anchor member 22 is secured in the adjacent vertebra 16. By way of example and not limitation, the anchor members 20, 22 may be top-loading, fixed and polyaxial pedicle screws, such as SILHOUETTE® pedicle screws, available from Zimmer Spine Inc., Edina, Minn. As is known in the art, the motion segment 12 facilitates spinal motion during extension and flexion motion as well as during lateral bending all while under axial loading. One or more components of the motion segment 12 can deteriorate from injury, disease, or age leading to severe pain. As such, treatment methods to stabilize the motion segment 12 may be necessary to relieve pain and restore a patient's mobility.

To that end, and with continued reference to FIG. 1, in an illustrative embodiment, a flexible member 24 is secured by and between the anchor members 20, 22. The flexible member 24 is secured to each anchor member 20, 22 to support that motion segment 12. A variety of means for securing the flexible member 24 to each of the anchor members 20, 22 will be apparent to those skilled in the art. For example, though not shown in FIG. 1, the flexible member 24 may be held in place by a set screw frictionally engaged with a ferrule placed over the flexible member 24. In another example, the flexible member 24 is compressed with a split bushing engaged by the set screw or a locking collar. As previously mentioned, the flexible member 24 may fit commercially available, top-loading, fixed and polyaxial pedicle screws, such as those designed to receive a variety of different diameter rigid fixation rods. The flexible member 24 provides stability, strength, and flexibility, without the rigidity of prior art rods, plates, and the like. The flexibility of the flexible member 24 may differ by design depending on the application and anatomical considerations. The flexible member 24 may be made, for example, of a flexible, homogenous material or a composite of different materials having differing elastic material properties, as will be discussed later. The flexible member 24 disclosed herein does not require intraoperative assembly and thus reduces operation time. For instance, the flexible member 24 may be provided in varying lengths, for example, twelve- or more inch lengths, so that a surgeon can cut, or shape, the flexible member 24 to fit appropriately between the anchor members 20, 22 along a specific section of the spine 10 or to accommodate/treat the recipient's disorder.

FIG. 2 depicts one embodiment of the flexible member 24 of FIG. 1. As shown in FIG. 2, the flexible member 24 includes an inner elastomeric member 26 and an outer fabric layer 28 situated securely around the inner elastomeric member 26. The flexible member 24 further includes an outer covering 30 and, in one embodiment, the outer covering 30 is an outer elastomeric member 32 situated securely around the outer fabric layer 28.

The inner elastomeric member 26, the outer fabric layer 28, and the outer elastomeric member 32 have a common lengthwise axis 34 and define a body 36 including opposing first 38 and second ends 40, with each opposing end 38, 40 configured for cooperation with one of the anchor members 20, 22. It will be appreciated that the inner elastomeric member 26 and the outer elastomeric member 32 are characterized as having a first elasticity and a second elasticity, respectively. In one embodiment, the second elasticity is different than the first elasticity to provide the flexible member 24 with the desired flexibility that may be optimized to treat a particular individual's disorder. For example, the second elasticity may be less than the first elasticity. By way of further example, the inner elastomeric member 26 may comprise polycarbonate based polyurethane (PCU) having a hardness of, for example, Shore durometer 75D. The outer elastomeric member 32 may be a similar material with a lower hardness. The outer fabric layer 28 may comprise, for instance, polyester, polypropylene, polyaramids, acrylics, polyacrylics, polyamides, polyethylene terephthalate, silks, carbon, graphite, highly oriented crystalline polyethylene fibers (for example, SPECTRA® 1000 and DYNEEMA®), combinations thereof or other fibers that may be bonded with the inner elastomeric member 26. Moreover, the outer fabric layer 28 may comprise a single or double knitted layer, braids, or non-wovens such as felts, unidirectional fiber layups, or random layups. In one embodiment, the outer fabric layer 28 provides tensile properties greater than the elastomeric members 26, 32 to allow for flexion of the flexible member 24 while maintaining the integrity of the flexible member 24.

The elasticity of each of the inner elastomeric member 26 and the outer elastomeric member 32 may be configured to affect the flexibility of the flexible member 24. In addition, the dimensions of each of the inner elastomeric member 26, the fabric layer 28, and the outer elastomeric member 32 can be adjusted to influence the desired flexibility of the flexible member 24. Furthermore, the shape of the inner elastomeric member 26 may also influence the desired flexibility. By way of example and not limitation, the inner elastomeric member 26 may be rod-shaped, as shown in FIG. 2, having a circular cross section, though the inner elastomeric member 26 may be another anatomically compatible shape such as a square, oval or rectangular cross-section. In another embodiment, the inner elastomeric member 26 may be rod-shaped with an aperture 42 extending therethrough to accept a guide wire which may facilitate percutaneous surgery. In addition, while the ends 38, 40 of the flexible member 24 are configured to cooperate with the anchor members 20, 22, at least one end 38, 40 may optionally have a penetrating obturator tip to facilitate insertion of the flexible member 24 through tissue. Thus, the overall shape of the flexible member 24 and the elasticity and dimensions of each of the inner elastomeric member 26, the fabric layer 28, and the outer elastomeric member 32 may be tailored to a recipient's anatomy, size, or diagnosis or even facilitate surgical installation.

Depending on the treatment selected for the recipient, the flexible member 24 may serve to support the motion segment 12 by, for example, reducing the load on the intervertebral disc 18 and/or facet joints. In addition, the separation of the adjacent vertebrae 14, 16 may be restored, for example, posterior distraction, to eliminate crushing or slipping of the disc 18 therebetween. Moreover, lordosis or klyphosis may be created/preserved where desired using the flexible member 24. Similarly, idiopathic scoliosis may be treated with one or more of the flexible members 24, as disclosed herein.

FIGS. 3 and 4 depict one method of making the flexible member 24 of FIG. 2. In one embodiment, the method includes placing and shrinking, for example, heat shrinking, a fabric member 44 about the inner elastomeric member 26 to securely situate the fabric member 44 therearound thereby defining the fabric layer 28. For example, with reference to FIG. 3, the outer diameter, $D_1$, of the fabric member 44 prior to heat shrinking is larger than the outer diameter, $D_2$, of the fabric layer 28 following heat shrinking.

Figure 5:
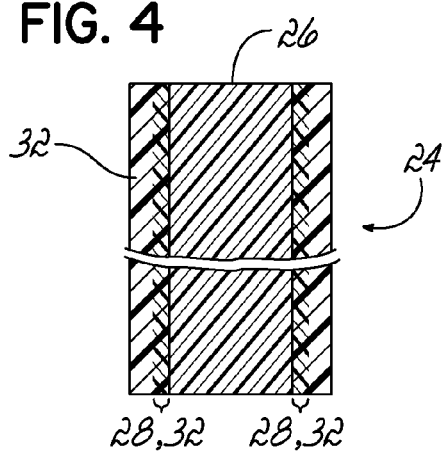
FIG. 5 is a partial cross-sectional view of one embodiment of the flexible member formed with the mold illustrated in FIG. 4.

In one embodiment, after heat shrinking, the fabric layer 28 and inner elastomeric member 26 are situated in a mold 46 as shown in FIG. 4. A liquefied elastomeric material 48 is introduced therein to surround the fabric layer 28. The liquefied elastomeric material 48 is solidified to provide the outer elastomeric member 32. The mold 46 may have two parts 46a, 46b, as shown, which separate or otherwise open after the liquefied elastomeric material 48 sets. In another embodiment, the liquefied elastomeric material 48 may penetrate the fabric layer 28 and contact the inner elastomeric member 26 to integrate the inner elastomeric member 26 with the fabric layer 28 and the outer elastomeric member 32. FIG. 5 illustrates a cross section of one embodiment of the flexible member 24 with the outer elastomeric member 32 penetrating into the fabric layer 28.

In another embodiment, after heat shrinking the fabric member 44 around the inner elastomeric member 26, the fabric layer 28 is coated with a solution that penetrates the fabric layer 28. One skilled in the art will observe that coating may comprise repeated dipping of the inner elastomeric member 26 and the fabric layer 28 in the solution to buildup the outer elastomeric member 32. The solution may facilitate securing the fabric layer 28 to the inner elastomeric member 26 or the solution may cover the fabric layer 28, possibly to prevent premature degradation thereof. In one embodiment, by varying a thickness of the outer elastomeric member 32 along the lengthwise axis 34, the flexibility of the flexible member 24 may vary from the first end 38 to the second end 40. If necessary, following heat shrinking the fabric member 44 or following providing the outer elastomeric member 32 to the fabric layer 28, the flexible member 24 may be annealed to relieve forming stresses.

Figure 7:
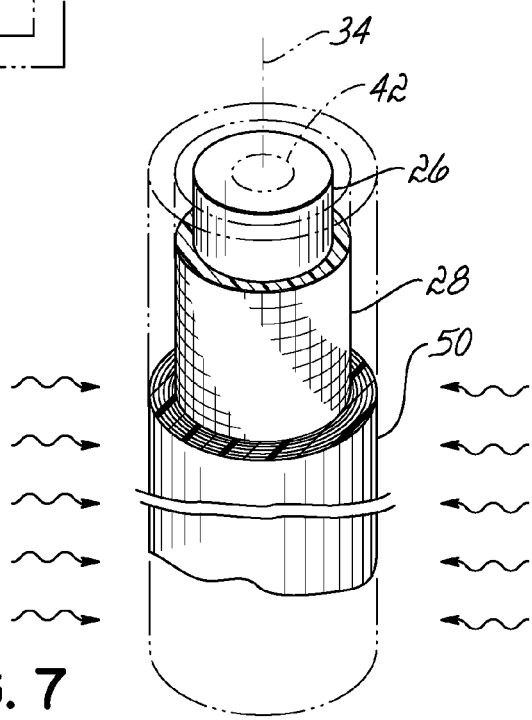
FIGS. 6 and 7 are partial perspective views of another method of forming the outer elastomeric member around the outer fabric layer and the inner elastomeric member of FIG. 2.
Figure 6:
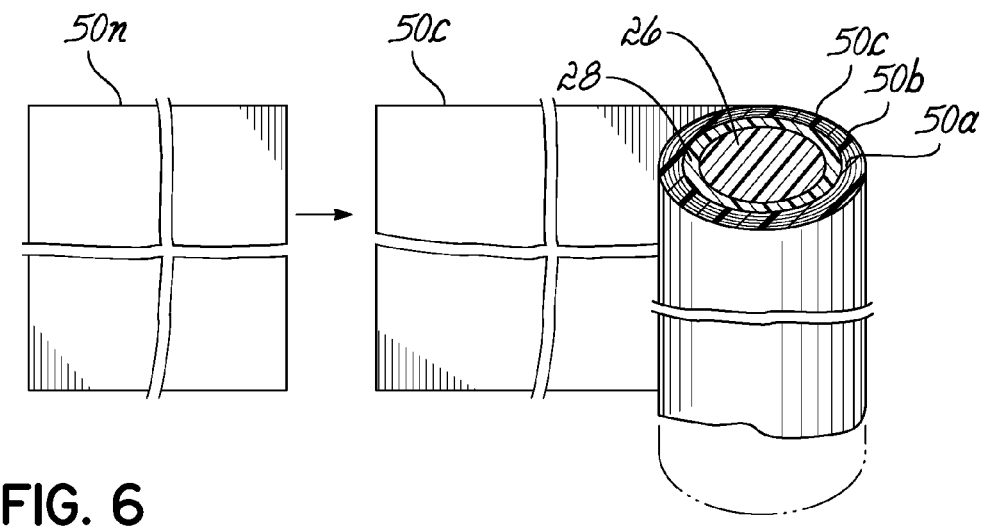

FIGS. 6 and 7 depict another method of making the flexible member 24 of FIG. 2. To that end, after heat shrinking the fabric member 44 around the inner elastomeric member 26, as shown in FIG. 3, a plurality of layers of material 50a, 50b, 50c . . . 50n (where "n" represents the $n^{th}$ layer) which may be, for example, elastomeric material, are rolled around the fabric layer 28 as shown in FIG. 6. Each layer of material 50a, 50b, 50c . . . 50n is then consolidated into a consolidated rolled layer 50 by additional heat treatment, as shown in FIG. 7. In one embodiment, each layer 50a, 50b, 50c, 50n may comprise a different elastomeric material, thus in one embodiment the construction of the flexible member 24 may provide a variable cross-section elasticity.

Figure 8:
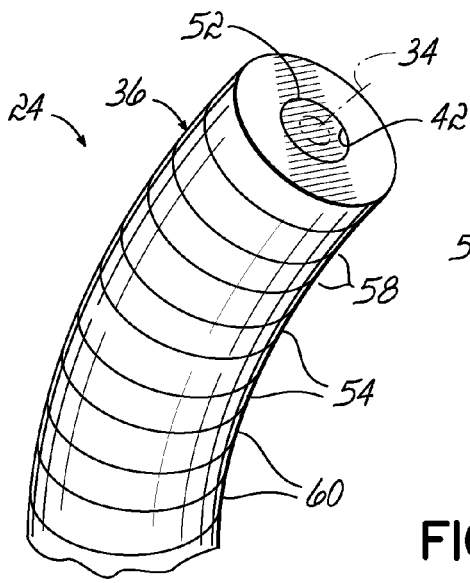
FIG. 8 is a partial perspective view of another embodiment of the flexible member having an elongated core member with a plurality of spaced-apart annular protrusions interspersed with a plurality of ring-shaped members.

Another embodiment of the flexible member 24 of FIG. 1 is shown in FIG. 8 and may be generally described as a flexible, heterogeneous composite rod. This flexible member 24 includes an elongated core member 52 including a plurality of spaced-apart annular protrusions 54 oriented perpendicular to the lengthwise axis 34 with each space between pairs of protrusions defining a circumferential groove 58. The flexible member 24 further includes a plurality of ring-shaped members 60 having a circular shape, for example. In alternative embodiments, other shapes for the ring-shaped members may be used such as square, oval, or rectangular cross-sections. Each one of the plurality of ring-shaped members 60 is securely situated about the elongated core member 52 within a respective circumferential groove 58.

Figure 11:
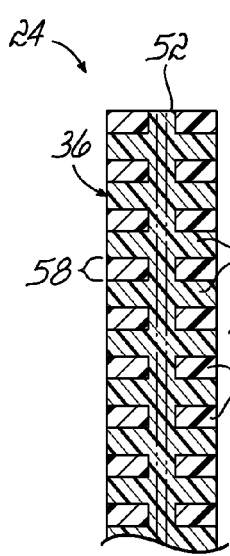
FIGS. 11 and 12 are partial cross-sections of embodiments of the flexible member of FIG. 8.

As shown more clearly in FIG. 11, the annular protrusions 54 alternate with the ring-shaped members 60 along the lengthwise axis 34 thereby defining the body 36. The body 36 includes opposing first and second ends 38, 40, (40 not shown for simplicity) with each end 38, 40 configured for cooperation with one anchor member 20, 22 as shown in FIG. 1. While it may appear in FIG. 11 that the thickness of each of the annular protrusions 54 are similar to the thickness of each of the ring-shaped members 60, the two thicknesses need not be similar. Furthermore, the thicknesses of the ring-shaped members 60 may vary from first end 38 to second end 40 or from each end 38, 40 into the center of the body 36. Similarly, the annular protrusion 54 need not be equal in thickness along the body 36 and may vary from one end to the other or from the ends 38, 40 into the center of the body 36.

The annular protrusions 54 and elongated core member 52 further define a monolith having a first elasticity. The ring-shaped members 60 have a second elasticity different than the first elasticity which may be combined with the thickness variation, as discussed previously, to provide a graduated flexibility along the lengthwise axis 34 of the flexible member 24. In one embodiment, the second elasticity is greater than the first elasticity, i.e., the ring-shaped member 60 comprises a material that is more flexible than that of the elongated core member 52. In another embodiment, the first elasticity is greater than the second elasticity, i.e., the elongated core member 52 and annular protrusions 54 comprise a material that is more flexible than that of the ring-shaped member 60. By way of example, the lower elastic material may comprise a biocompatible metal such as stainless steel, titanium, or nitinol, or polymers such as polysulfone, polimide, PEEK, Ultra PAEK, or Shore 75D PCU. The higher elastic material may comprise polyurethane, silicone, or other biocompatible, low modulus material.

Similar to the embodiments of the flexible member 24 illustrated in FIG. 2, embodiments of the flexible member 24 illustrated in FIG. 8 may have a rod-shape, as shown, though the shape of the body 36 is not limited thereto. In another embodiment, the body 36 includes the aperture 42 extending therethrough which may be utilized during a percutaneous procedure, as previously described.

Figure 9:
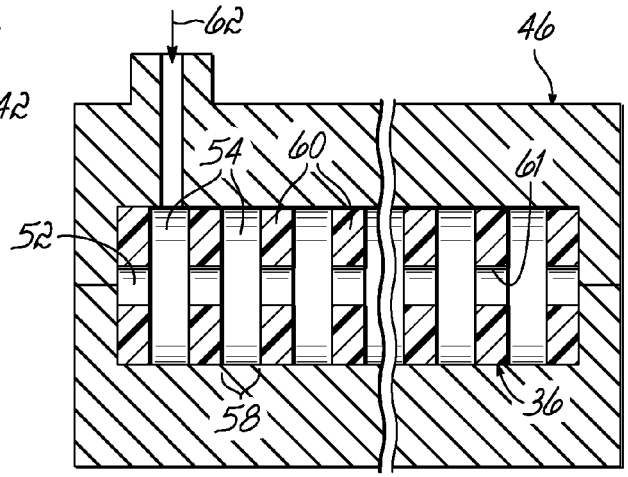
FIGS. 9 and 10 are diagrammatic cross-sectional views of methods of forming the flexible member of FIG. 8 with a mold.

With reference to FIG. 9, another method of making the flexible member 24 of FIG. 8 includes aligning the ring-shaped members 60 in the mold 46. Each ring-shaped member 60 includes a central aperture 61. The ring-shaped members 60 may be oriented perpendicular to the lengthwise axis 34. The spaces between the ring-shaped members 60 and apertures 61 are filled with the liquefied material 62. The liquefied material 62 is then solidified to define the body 36, as shown in FIG. 11.

Figure 10:
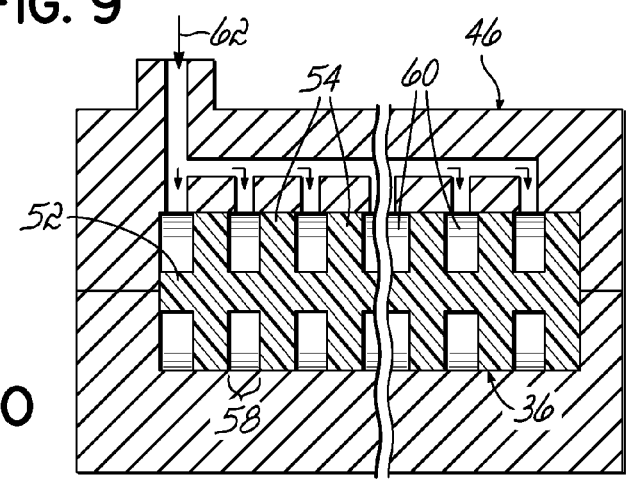
Figure 12:
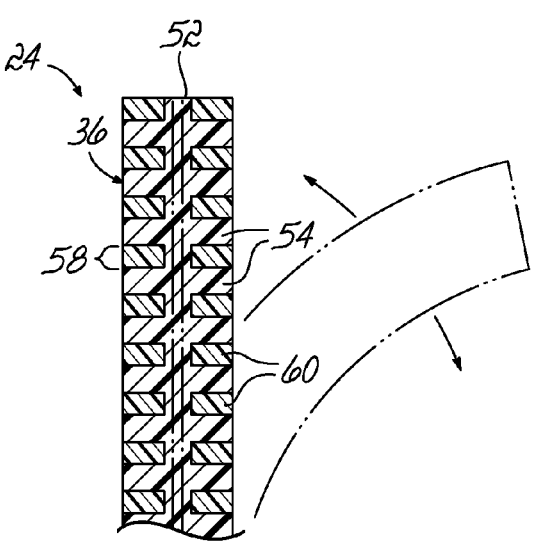

FIG. 10 depicts another method of making the flexible member 24 of FIG. 8. One embodiment of the method includes providing the elongated core member 52 with spaced-apart circumferential grooves 58 about the lengthwise axis 34 thereof to define the spaced-apart annular protrusions 54 oriented perpendicular to the lengthwise axis 34. Such elongated core member 52 may be formed, for example, via injection molding or by being lathed from a solid elongated core. The elongated core member 52 is situated in the mold 46 and the grooves 58 are filled with a liquefied material 62. The liquefied material 62 is solidified to provide the ring-shaped members 60 as shown in FIG. 12. Each one of the ring-shaped members 60 is securely situated about the elongated core member 52 within a respective circumferential groove 58 and adjacent corresponding annular protrusions 54 thereby defining the body 36. The annular protrusions 54 and the elongated core member 52 define a monolith having a first elasticity. The ring-shaped members 60 each have a second elasticity. The second elasticity may be different than the first elasticity. As shown in FIG. 12, the combination of the first and second elasticities may be tailored to provide the flexible member 24 with a desired flexibility.

Figure 13:
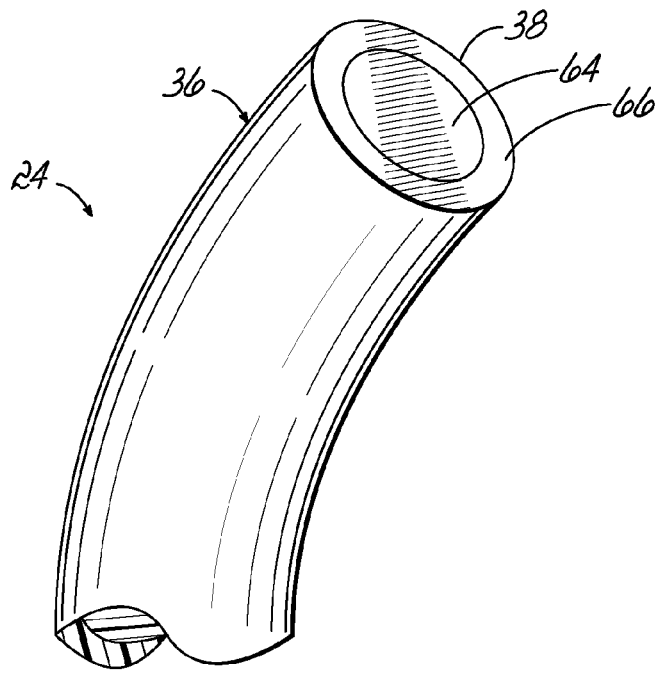
FIG. 13 is a partial perspective view of another embodiment of the flexible member with an elongated polymeric member and outer NiTiNOL jacket.

Another exemplary embodiment of the flexible member 24 is illustrated in FIG. 13. In this embodiment the flexible member 24 includes an elongated polymeric member 64 and an outer nitinol member 66 situated securely around the elongated polymeric member 64. The elongated polymeric member 64 and outer nitinol member 66 define the body 36 including opposing first and second ends 38, 40, (40 not shown for simplicity) with each opposing end 38, 40 configured for cooperation with one anchor member 20, 22 (shown in FIG. 1). The elongated polymeric member 64 further has a first elasticity and the outer nitinol member 66 has a second elasticity different than the first elasticity to provide the flexible member 24 with a desired flexibility. By way of example, the elongated polymeric member 64 may comprise similar materials as the inner elastomeric member 26 described previously with respect to FIGS. 2 and 8. In one embodiment, the first elasticity is greater than the second elasticity. In another embodiment, the second elasticity is greater than the first elasticity. By way of example, the outer nitinol member 66 may be one or more other shape memory alloys that are biocompatible. Similar to the previous embodiments, the thickness of the outer nitinol member 66 may be varied.

Figure 14:
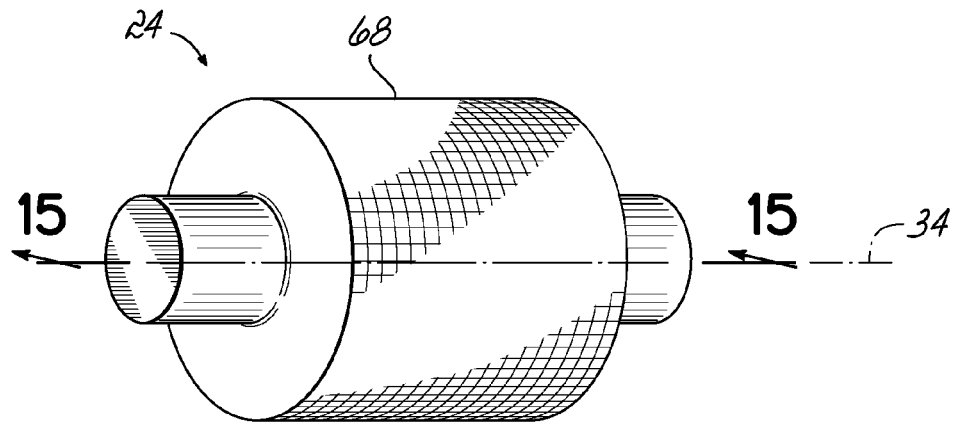
FIGS. 14 and 15 depict a perspective view and a cross-sectional view, respectively, of another embodiment of the flexible member with a central core that extends beyond an outer core and having a cover covering both the central core and the outer core.
Figure 15:
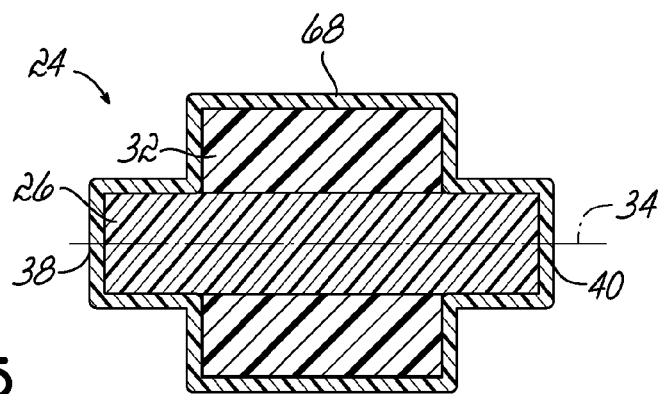

In yet another embodiment, as shown in FIGS. 14 and 15, the flexible member 24 comprises the inner elastomeric member 26 and the outer elastomeric member 32 wherein the inner elastomeric member 26 extends or projects along the lengthwise axis 34 beyond the outer elastomeric member 32. In addition, a cover 68 encloses the inner elastomeric member 26 and the outer elastomeric member 32. Thus, as shown in FIG. 15, the opposing ends 38, 40 comprise the inner elastomeric member 26 enclosed with the cover 68. As shown in FIGS. 14 and 15, in one embodiment, the inner elastomeric member 26 with the cover 68 is sized to cooperate with the anchor members 20, 22 (shown in FIG. 1). With reference to FIGS. 1, 14, and 15, by way of example, the outer elastomeric member 32 may provide only compressive support to the motion segment 12. In other words, and with reference to FIG. 1, as the anchor members 20, 22 approach one another due to compression of the disc 18, only the inner elastomeric member 26 of FIG. 15 compresses. With continued reference to FIG. 15, it is notable, however, that the outer elastomeric member 32 may support the inner elastomeric member 26 during this motion by preventing the inner elastomeric member 26 from bowing. Once the adjacent vertebrae 14, 16 reach a distance approximately the length of the outer elastomeric member 32, the anchor members 20, 22 may contact the outer elastomeric member 32. At this point the outer elastomeric member 32 may begin to compress thereby providing additional compressive support to the disc 18.

In accordance with the principles disclosed herein is a method for treating the spine 10 of a patient. The method comprises assessing the patient's spine, for example, by x-ray or MRI imaging, as are known in the art. With the patient's spine assessment in mind, the practitioner may select one of a plurality of implants 70 each having different elastic characteristics for implantation and attachment to one or more bone anchors or anchor members 20, 22, as depicted in FIG. 1. In one embodiment, the implant 70 is at least a portion of the flexible member 24, described above. For example, the practitioner may select a flexible member 24 and trim or cut the flexible member 24 to length for implantation between the bone anchors. In another embodiment, the implant 70 is made per the methods for making the flexible member 24, described herein, according to the assessment. In yet another embodiment and with reference to FIG. 3, the implant 70 comprises an inner portion 72 of one elastomeric material and an outer portion 74 of another or second elastomeric material. It will be appreciated that the inner and outer portions 72, 74 may have different elastomeric properties, for example, the elasticity of the inner portion 72 may be greater than the elasticity of the outer portion 74. Thus, the elastic properties of the implant 70 may be controlled or customized for a particular patient. While the elastic properties may be individually tailored, one skilled in the art will appreciate that the implant 70 may be manufactured such that a variety of implants with graduated increments of elasticity are readily available.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative method and illustrative examples shown and described. Accordingly, departures may be made from such details without departing from the scope of the general inventive concept.

What is claimed is:

1. A spinal stabilization system for use in stabilizing a spinal column comprising:
a first anchor member configured to be secured to a first vertebra;
a second anchor member configured to be secured to a second vertebra;
a flexible member securable between the first anchor and the second anchor, the flexible member including an inner elastomeric member and an outer fabric layer situated securely around the inner elastomeric member, the outer fabric layer formed of a plurality of interwoven filaments, the inner elastomeric member and the outer fabric layer having a common lengthwise axis and defining a body including opposing first and second ends, with each opposing end configured for cooperation with an anchor member, the inner elastomeric member further having a first elasticity to provide the flexible member with a desired flexibility and having tensile properties to allow for flexion of the flexible member; and
an outer covering defining an outer elastomeric member situated securely around the outer fabric layer with the inner elastomeric member, the outer fabric layer, and the outer elastomeric member having the common lengthwise axis and defining the body including the opposing first and second ends, the outer elastomeric member having a second elasticity that is less than the first elasticity.

2. The spinal stabilization system of claim 1 wherein the outer elastomeric member penetrates the outer fabric layer and contacts the inner elastomeric member to integrate the inner elastomeric member, the outer fabric layer, and the outer elastomeric member.

3. The spinal stabilization system of claim 1 wherein the inner elastomeric member is rod-shaped.

4. The spinal stabilization system of claim 1 wherein the inner elastomeric member includes an aperture extending therethrough along a length thereof.

5. A spinal stabilization system, comprising:
a first anchor member configured to be secured to a first vertebra;
a second anchor member configured to be secured to a second vertebra; and
a flexible member securable between the first anchor member and the second anchor member;
the flexible member comprising:
an inner elastomeric member;
an outer fabric layer formed of a plurality of interwoven fibers situated securely around the inner elastomeric member; and
an outer elastomeric member surrounding the outer fabric layer; the outer elastomeric member having an elasticity that is different than an elasticity of the inner elastomeric member;
wherein the inner elastomeric member and the outer fabric layer have a common lengthwise axis and are coextensive extending between opposing first and second ends of the flexible member.

6. The spinal stabilization system of claim 5, wherein the flexible member further comprises an outer covering around the outer fabric layer.

7. The spinal stabilization system of claim 6, wherein the outer covering is coextensive with the inner elastomeric member and the outer fabric layer such that the outer covering extends from the first end to the second end of the flexible member.

8. The spinal stabilization system of claim 5, wherein the flexible member is not intra-operatively assembled.

9. A spinal stabilization system, comprising:
a first anchor member configured to be secured to a first vertebra;
a second anchor member configured to be secured to a second vertebra; and
a flexible member securable between the first anchor member and the second anchor member;
the flexible member comprising:
an inner elastomeric member;
an outer fabric layer situated securely around the inner elastomeric member; and
an outer elastomeric member surrounding the outer fabric layer; the outer elastomeric member having an elasticity that is different than an elasticity of the inner elastomeric member;
wherein the inner elastomeric member and the outer fabric layer have a common lengthwise axis and are coextensive extending between opposing first and second ends of the flexible member; and
wherein the outer fabric layer is a fabric member heat shrunk around the inner elastomeric member.

* * * * *